US008552051B2

(12) United States Patent
Harvey et al.

(10) Patent No.: US 8,552,051 B2
(45) Date of Patent: *Oct. 8, 2013

(54) USE OF PHARMACEUTICAL COMPOSITIONS CONTAINING MESEMBRENONE

(75) Inventors: Alan Harvey, Glasgow (GB); Nigel Gericke, Cape Town (ZA); Alvaro Viljoen, Cresta (ZA)

(73) Assignee: H. L. Hall & Sons Limited (ZA)

( * ) Notice: Subject to any disclaimer, the term of this patent is extended or adjusted under 35 U.S.C. 154(b) by 0 days.

This patent is subject to a terminal disclaimer.

(21) Appl. No.: 13/256,686

(22) PCT Filed: Mar. 16, 2010

(86) PCT No.: PCT/IB2010/051132
§ 371 (c)(1),
(2), (4) Date: Oct. 31, 2011

(87) PCT Pub. No.: WO2010/106494
PCT Pub. Date: Sep. 23, 2010

(65) Prior Publication Data
US 2012/0041045 A1 Feb. 16, 2012

(30) Foreign Application Priority Data
Mar. 20, 2009 (ZA) ................ 2009/02003

(51) Int. Cl.
*A61K 31/403* (2006.01)
(52) U.S. Cl.
USPC ........... 514/412; 548/452; 548/570; 548/571; 548/577
(58) Field of Classification Search
USPC .......... 514/421, 412; 548/452, 512, 570, 571, 548/577
See application file for complete search history.

(56) References Cited

U.S. PATENT DOCUMENTS

| | | | |
|---|---|---|---|
| 6,271,001 B1 | 8/2001 | Clarke | |
| 6,288,104 B1 | 9/2001 | Gericke et al. | |
| 2002/0106731 A1 | 8/2002 | Ruben et al. | |
| 2004/0185429 A1 | 9/2004 | Kelleher-Andersson et al. | |
| 2004/0229291 A1 | 11/2004 | Zhou et al. | |
| 2004/0254152 A1 | 12/2004 | Monje et al. | |
| 2005/0004046 A1 | 1/2005 | Praag | |
| 2005/0009742 A1 | 1/2005 | Bertilsson et al. | |
| 2005/0009847 A1 | 1/2005 | Bertilsson et al. | |
| 2005/0031538 A1 | 2/2005 | Steindler et al. | |
| 2005/0032702 A1 | 2/2005 | Eriksson | |
| 2012/0004275 A1 | 1/2012 | Gericke et al. | |

FOREIGN PATENT DOCUMENTS

| | | |
|---|---|---|
| DE | 3604112 A1 | 8/1987 |
| WO | 9746234 A1 | 12/1997 |
| WO | 02092112 A1 | 11/2002 |
| WO | WO2006/025920 * | 3/2006 |
| WO | 2010106495 A1 | 9/2010 |

OTHER PUBLICATIONS

Definition of Prevent, Princeton University "About WordNet." WordNet. Princeton University. 2010. <http://wordnet.princeton.edu>, accessed Sep. 18, 2012.*
Zhang et al. Expert Opin. Ther. Targets 2005, 9 (6), 1283-1305.*
Lang et al. Asthma, in Disease Management Project, Cleveland Clinic Center for Continuing Education, published Aug. 1, 2010, <http://www.clevelandclinicmeded.com/medicalpubs/diseasemanagement/allergy/bronchial-asthma/>, accessed Oct. 10, 2012.*
Gericke, et al., "*Sceletium*—a review update," *Journal of Ethnopharmacology*, 119(3):653-663 (2008).
Napoletano, et al., Mesembrine is an inhibitor of PDE4 that follows the structure-activity relationship of rolipram, *Chemistry Preprint Archive*, vol. 2001, Issue 3, Mar. 2001, pp. 303-308.
Patnala, et al., "A capillary zone electrophoresis method for the assay and quality control of mesembrine in *Sceletium* tablets," *Journal of Pharmaceutical and Biomedical Analysis*, 48(2):440-446 (2008).
Patnala, et al., "Investigations of the phytochemical content of *Sceletium tortuosum* following the preparation of Kougoed" by fermentation of plant material, *J. Ethnopharmacol.*, 121(1);86-91 (2009).
Saldou, et al., Comparison of recombinant human PDE4 isoforms: interaction with substrate and inhibitors, *Cell Signal.*, 10: 427-440 (1998).
Schmeda-Hirschmann, et al., "Activity of Amaryllidaceae alkaloids on the blood pressure of normotensive rates," *Pharmacy and Pharmacology Communications*, 6(7):309-313 (2000).
Smith, et al., "The distribution of mesembrine alkaloids in selected taxa of the Mesembryanthemaceae and their modification in the *Sceletium* derived kougoed," *Pharmaceutical Biology*, Swets and Zeitlinger, Misse, NL, 36(3):173-179 (1998).
Smith, et al., "Psychoactive Constituents of the Genus *Sceletium* N.E. Br. and Other Mesembryanthemaceae: A Review," *Journal of Ethnopharmacology*, Elsevier Scientific Publishers Ltd., 50(3):119-130 (1996).
Tatsumi, et al., "Pharmacological profile of neuroleptics at human monoamine transporters," *Eur. J. Pharmacol.*, 368:277-283 (1999).
Van WYK, "A broad view of commercially important southern African medicinal plants," Journal of Ethnopharmacology, 119(3):342-355 (2008).

(Continued)

*Primary Examiner* — Sreeni Padmanabhan
*Assistant Examiner* — Irina Neagu
(74) *Attorney, Agent, or Firm* — Kilpatrick Townsend & Stockton LLP

(57) ABSTRACT

The use of mesembrenone and medicaments and dietary supplements containing mesembrenone. The applicant has surprisingly found that mesembrenone exhibits potent PDE-4 inhibition properties and, in addition to being useful in treating conditions that respond to treatment with a PDE-4 inhibitor, has dual activity on account of its serotonin-uptake inhibition properties. Mesembrenone is extracted and isolated, for example as a pure compound, from plant material of the plant family Mesembryanthemaceae. Preferably a plant or plants from the genus *Sceletium*, more preferably, *Sceletium tortuosum*(L) N.E.Br is used.

19 Claims, 2 Drawing Sheets

(56) References Cited

OTHER PUBLICATIONS

Weniger, et al., "Cytotoxic activity of amaryllidaceae alkaloids," Planta Medica, 61(1):77-79 (1995).
International Search Report dated Jun. 2, 2010 in Application No. PCT/IB2010/051132.
International Search Report dated Sep. 2, 2010 in Application No. PCT/IB2010/051133.
Response to Office Action filed May 6, 2013, in U.S. Appl. No. 13/256,674.
Office Action dated Jun. 13, 2012, in related U.S. Appl. No. 13/256,674.
Response to Jun. 13, 2012 Office Action in related U.S. Appl. No. 13/256,674.
Office Action dated Nov. 6, 2012, in related U.S. Appl. No. 13/256,674.
Harvey, et al., "Pharmacological actions of the South African medicinal and functional food plant *Sceletium tortuosum* and its principal alkaloids", Journal of Ethnopharmacology, 2011, 137, 1124-1129.
Final Office Action in related U.S. Appl. No. 13/256,674 dated Jul. 19, 2013, 16 pages.

\* cited by examiner

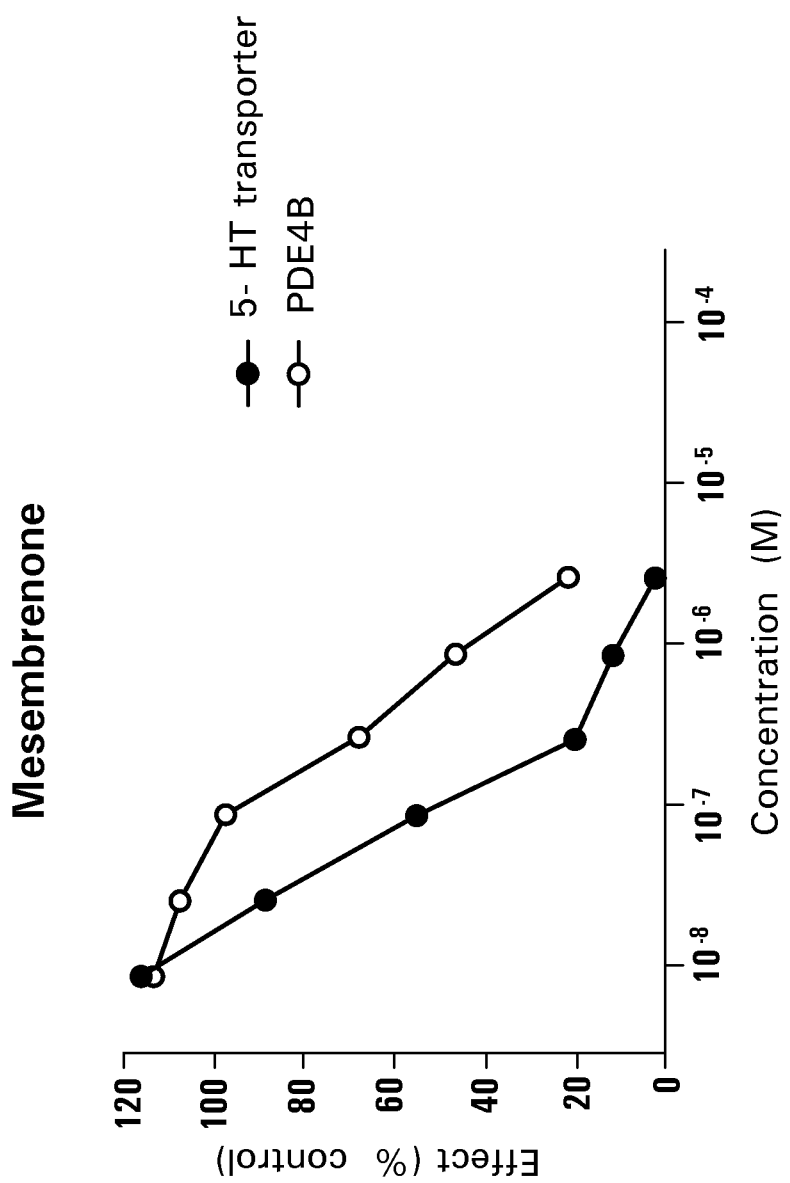

USE OF PHARMACEUTICAL COMPOSITIONS CONTAINING MESEMBRENONE

CROSS REFERENCE TO RELATED APPLICATIONS

This application is the U.S. national phase of International Application No. PCT/IB2010/051132 filed on Mar. 16, 2010 and published in English on Sep. 23, 2010 as International Publication No. WO 2010/106494 A1, which application claims priority to South African Patent Application No. 2009/02003 filed on Mar. 20, 2009, the contents of both of which are incorporated herein by reference.

FIELD OF THE INVENTION

This invention relates to pharmaceutical uses of mesembrenone and medicaments and dietary supplements containing mesembrenone.

BACKGROUND TO THE INVENTION

The plants of the genus *Sceletium* are known to contain indole alkaloids such as mesembrenol, mesembranol, mesembrine and mesembranone, the chemical formulae of which are described in U.S. Pat. No. 6,288,104. U.S. Pat. No. 6,288,104 describes mesembrine, mesembrenol and mesembranone as having potent 5-HT uptake inhibitory activity and, thus, as being useful in treating conditions that respond to treatment with a serotonin-uptake inhibitor, such as mild to moderate depression. Mesembrine hydrochloride has previously been reported to be a weak PDE4 inhibitor (Napoletano, M. et al. 2001. Mesembrine is an inhibitor of PDE4 that follows the structure-activity relationship of rolipram. Chemistry Preprint Archive, Volume 2001, Issue 3, Mar. 2001, Pages 303-308).

The applicant has surprisingly found that mesembrenone exhibits potent PDE-4 inhibition properties and, in addition to being useful in treating conditions that respond to treatment with a PDE-4 inhibitor, has dual activity on account of its serotonin-uptake inhibition properties.

SUMMARY OF THE INVENTION

According to one aspect of the invention, there is provided the use of mesembrenone, or a pharmaceutically acceptable salt thereof, in the manufacture of a medicament or dietary supplement for preventing or treating a condition that responds to treatment with a PDE-4 inhibitor.

It will be appreciated that mesembrenone may be utilized in either of its diastereoisomeric forms, or a mixture thereof.

In an embodiment of the invention, mesembrenone is extracted and isolated, for example as a pure compound, from plant material of the plant family Mesembryanthemaceae, preferably a plant or plants from the genus *Sceletium*, more preferably, a plant or plants of the species *Sceletium tortuosum*(L.) N.E.Br.

Mesembrenone may also be synthesised by those skilled in the art according to known processes.

In another embodiment of the invention, mesembrenone may be used in the form of an extract from plant material of the plant family Mesembryanthemaceae, preferably a plant from the genus *Sceletium*, more preferably, a plant of the species *Sceletium tortuosum*(L.)N.E.Br. The plant extract may be enriched in mesembrenone, according to methods known in the art.

Thus, mesembrenone may be in the form of an isolated pure compound or plant extract. Mesembrenone may be used in free form or in the form of a pharmaceutically acceptable salt, e.g. an acid addition salt, e.g. obtained by addition of an inorganic or organic acid, e.g. a hydrochloride acid addition salt.

According to the invention there is also provided a method of preventing, alleviating or treating a mammal suffering from a condition which method includes administering to said patient a therapeutically effective amount of mesembrenone or a pharmaceutically acceptable salt thereof wherein said condition responds to the prevention, alleviation, modulation or treatment with a PDE-4 inhibitor.

According to the invention, mesembrenone or a pharmaceutically acceptable salt thereof has activity as a pharmaceutical, in particular as a modulator of PDE 4 enzyme activity, and may be used in the prevention and treatment of the following conditions, and included in pharmaceuticals and supplements for the prevention and treatment of the following conditions:

Respiratory tract conditions: obstructive diseases of the airways including: asthma, including bronchial, allergic, intrinsic, extrinsic, exercise-induced, drug-induced (including aspirin and NS AID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

Bone and joints conditions: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

Pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

Skin conditions: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

Eye conditions: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

Gastrointestinal tract conditions: glossitis, gingivitis, periodontitis; oesophagitis, including reflux; eosinophilic gastroenteritis, mastocytosis, Crohn's disease, colitis including ulcerative colitis, microscopic colitis, indeterminant colitis proctitis, pruritis ani; irritable bowel disorder, coeliac disease, irritable bowel syndrome, non-inflammatory diarrhea and food-related allergies which may have effects remote from the gut (for example migraine, rhinitis or eczema);

Abdominal conditions: hepatitis, including autoimmune, alcoholic and viral; fibrosis and cirrhosis of the liver; cholecystitis; pancreatitis, both acute and chronic;

Genitourinary conditions: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvovaginitis; Peyronie's disease; erectile dysfunction (both male and female);

Allograft resection: acute and chronic following, for example, transplantation of kidney, heart, liver, lung, bone marrow, skin or cornea or following blood transfusion; or chronic graft versus host disease;

CNS conditions: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HTV-associated neuropathies; neurosarcoidosis; central and peripheral nervous system complications of malignant, infectious or autoimmune processes, disorders of cognition, learning and memory, anxiety, depression, Parkinsons Disease, Other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome; 12. other disorders with an inflammatory or immunological component; including acquired immune deficiency syndrome (AIDS), leprosy, Sezary syndrome, and paraneoplastic syndromes;

Cardiovascular conditions: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

Oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

The preferred indications are asthma, COPD, rhinitis, osteoarthritis, rheumatoid arthritis, psoriasis, eczema, ulcerative colitis, Crohns Disease, Alzheimers disease, multiple sclerosis, Parkinsons disease, disorders of cognition, learning, memory, anxiety and depression, and chronic pain.

The invention also extends to a method of preventing or treating in a subject conditions that respond to treatment with simultaneous administration of a serotonin-uptake inhibitor and a PDE-4 inhibitor, comprising administering to said subject a therapeutically effective amount of mesembrenone or a pharmaceutically acceptable salt thereof as hereinbefore described.

The novel and unexpected potent dual 5-HT uptake inhibition and PDE4 inhibition by mesembrenone or a pharmaceutically acceptable salt thereof has a wide range of useful animal and human health applications.

Thus, on account of its 5-HT uptake inhibitory activity mesembrenone or a pharmaceutically acceptable salt thereof may be used in the manufacture of a medicament having a dual 5-HT uptake inhibitory activity and PDE4 inhibitory activity.

More particularly, as a result of this dual activity the medicament may be used in treating or alleviating diseases or conditions such as e.g. arthritis including rheumatoid arthritis, inflammatory bowel disease including ulcerative colitis, autoimmune diseases, asthma, rhinitis, eczema, psoriasis, chronic obstructive pulmonary disease, Alzheimers Disease, neurodegenerative diseases, multiple sclerosis, psychotic states, deficits in learning, memory, cognition, anxiety, depression or eating disorders.

A further non-limiting example is the application of mesembrenone or a pharmaceutically acceptable salt thereof to conditions of the central and peripheral nervous system that respond to stimulating or increasing neurogenesis, since neuoregenesis is known to be enhanced either by a 5-HT uptake inhibitor or by a PDE4 inhibitor.

Conditions that can be beneficially treated by increasing or stimulating neurogenesis are known in the art (see for example U.S. Patent Application Publication Nos. 20020106731, 2005/0009742 and 2005/0009847, 20050032702, 2005/0031538, 2005/0004046, 2004/0254152, 2004/0229291, and 2004/0185429, herein incorporated by reference in their entirety).

Accordingly, mesembrenone or a pharmaceutically acceptable salt thereof may be useful in the treatment of diseases characterized by pain, addiction, and/or depression by directly replenishing, replacing, and/or supplementing neurons and/or glial cells and/or enhancing the growth and/or survival of existing neural cells, and/or slowing or reversing the loss of such cells in a neurodegenerative condition.

According to the invention there is provided a method of contacting a neural cell with mesembrenone or a pharmaceutically acceptable salt thereof in order to increase neurodifferentiation. The method may be used to stimulate a neural cell for proliferation, and thus neurogenesis, via one or more other agents used with mesembrenone in combination, or to maintain, stabilize, stimulate, or increase neurodifferentiation in a cell or tissue by use of mesembrenone.

The invention also provides a method comprising contacting the cell or tissue with mesembrenone or a pharmaceutically acceptable salt thereof. In some embodiments, the cell or tissue is in an animal subject or a human patient as described herein. Non-limiting examples include a human patient treated with chemotherapy and/or radiation, or other therapy or condition which is detrimental to cognitive function; or a human patient diagnosed as having epilepsy, a condition associated with epilepsy, or seizures associated with epilepsy.

Administration of mesembrenone may be before, after, or concurrent with another condition, or therapy.

Uses of Mesembrenone or a Pharmaceutically Acceptable Salt Thereof in Neurogenesis Embodiments of a first aspect of the invention include a method of modulating neurogenesis by contacting one or more neural cells with mesembrenone. The amount of mesembrenone or a pharmaceutically acceptable salt thereof may be selected to be effective to produce an improvement in a treated subject, or to allow for the detection of neurogenesis in vitro. In some embodiments, the amount is one that also minimizes clinical side effects or drug interactions seen with administration to a subject.

Without being bound by theory, and offered to improve the understanding of the disclosure, phosphodiesterase inhibition is believed to promote neurogenesis by targeting second messenger systems downstream of neurotransmitters and other signaling molecules. Cyclic adenosine monophosphate (cAMP) and cyclic guanosine monophosphate (cGMP) are both examples of such second messengers, and inhibition of PDEs may prolong cAMP and cGMP signals and may increase signaling through neurogenic signal transduction pathways.

Cognitive Function

In other embodiments, and if compared to a reduced level of cognitive function, a method of the invention may be for enhancing or improving the reduced cognitive function or to maintain or stabilize the cognitive function in a subject or patient. The method may comprise administering mesembrenone to a subject or patient to enhance or improve a decline or decrease of cognitive function due to a therapy and/or condition that reduces cognitive function. In some embodiments, the maintenance or stabilization of cognitive function may be at a level, or thereabouts, present in a subject or patient in the absence of a therapy and/or condition that reduces cognitive function or as a result of a therapy and/or condition that reduces cognitive function.

These methods optionally include assessing or measuring cognitive function of the subject or patient before, during, and/or after administration of the treatment to detect or determine the effect thereof on cognitive function. So in one embodiment, a methods may comprise i) treating a subject or patient that has been previously assessed for cognitive function and ii) reassessing cognitive function in the subject or patient during or after the course of treatment. The assessment may measure cognitive function for comparison to a control or standard value (or range) in subjects or patients in the absence of mesembrenone. This may be used to assess the efficacy of mesembrenone in alleviating the reduction in cognitive function.

Mood Disorders

In other embodiments, there is provided a method of treating a mood disorder in a subject or patient comprising administering a therapeutically effective amount of mesembrenone or a pharmaceutically acceptable salt thereof to a subject or patient that is under treatment with a therapy and/or in a condition that results in a mood disorder. Non-limiting examples of mood disorders include depression, anxiety, hypomania, panic attacks, excessive elation, seasonal mood (or affective) disorder, schizophrenia and other psychoses, lissencephaly syndrome, anxiety syndromes, anxiety disorders, phobias, stress and related syndromes, aggression, non-senile dementia, post-pain depression, and combinations thereof.

Identification of Subjects and Patients

The invention includes methods comprising identification of an individual suffering from one or more disease, disorders, or conditions, or a symptom thereof, and administering to the subject or patient a therapeutically effective amount mesembrenone or a pharmaceutically acceptable salt thereof. The identification of a subject or patient as having one or more diseases, disorders or conditions, or a symptom thereof, may be made by a skilled practitioner using any appropriate means known in the field.

The Subsequent Administration of Mesembrenone by the Identification or Diagnosis of a Subject or Patient in Need of One or More Effects Provided by Mesembrenone Non-limiting examples of an effect include neurogenic activity and/or potentiation of neurogenesis.

In some embodiments, identification of a patient in need of neurogenesis modulation comprises identifying a patient who has or will be exposed to a factor or condition known to inhibit neurogenesis, including but not limited to, stress, aging, sleep deprivation, hormonal changes (e.g., those associated with puberty, pregnancy, or aging (e.g., menopause), lack of exercise, lack of environmental stimuli (e.g., social isolation), diabetes and drugs of abuse (e.g., alcohol, especially chronic use; opiates and opioids; psychostimulants). In some cases, the patient has been identified as non-responsive to treatment with primary medications for the condition(s) targeted for treatment (e.g., non-responsive to antidepressants for the treatment of depression), and mesembrenone is administered in a method for enhancing the responsiveness of the patient to a co-existing or pre-existing treatment regimen.

In additional embodiments, the patient in need of neurogenesis modulation suffers from premenstrual syndrome, post-partum depression, or pregnancy-related fatigue and/or depression, and the treatment comprises administering a therapeutically effective amount of mesembrenone. Without being bound by any particular theory, and offered to improve understanding of the invention, it is believed that levels of steroid hormones, such as estrogen, are increased during the menstrual cycle during and following pregnancy, and that such hormones can exert a modulatory effect on neurogenesis.

In some embodiments, the patient is a user of a recreational drug including but not limited to alcohol, amphetamines, PCP, cocaine, and opiates. Without being bound by any particular theory, and offered to improve understanding of the invention, it is believed that some drugs of abuse have a modulatory effect on neurogenesis, which is associated with depression, anxiety and other mood disorders, as well as deficits in cognition, learning, and memory. Moreover, mood disorders are causative and/or risk factors for substance abuse, and substance abuse (as self-medication) is a common behavioral symptom of mood disorders. Thus, substance abuse and mood disorders may reinforce each other, rendering patients suffering from both conditions non-responsive to treatment. Thus, in some embodiments, mesembrenone or a pharmaceutically acceptable salt thereof may be used to treat patients suffering from substance abuse and/or mood disorders.

In further embodiments, the patient is on a co-existing and/or pre-existing treatment regimen involving administration of one or more prescription medications having a modulatory effect on neurogenesis. For example, in some embodiments, the patient suffers from chronic pain and is prescribed one or more opiate/opioid medications; and/or suffers from ADD, ADHD, or a related disorder, and is prescribed a psychostimulant, such as ritalin, dexedrine, adderall, or a similar medication which inhibits neurogenesis. Without being bound by any particular theory, and offered to improve understanding of the invention, it is believed that such medications can exert a modulatory effect on neurogenesis, leading to depression, anxiety and other mood disorders, as well as deficits in cognition, learning, and memory. Thus, in some preferred embodiments, mesembrenone or a pharmaceutically acceptable salt thereof is administered to a patient who is currently or has recently been prescribed a medication that exerts a modulatory effect on neurogenesis, in order to treat depression, anxiety, and/or other mood disorders, and/or to improve cognition.

In additional embodiments, the patient suffers from chronic fatigue syndrome; a sleep disorder; lack of exercise (e.g., elderly, infirm, or physically handicapped patients); and/or lack of environmental stimuli (e.g., social isolation); and the treatment comprises administering a therapeutically effective amount of mesembrenone or a pharmaceutically acceptable salt thereof.

In more embodiments, the patient is an individual having, or who is likely to develop, a disorder relating to neural degeneration, neural damage and/or neural demyelination.

In further embodiments, a subject or patient includes human beings and animals in assays for behavior linked to neurogenesis. Exemplary human and animal assays are known to the skilled person in the field.

In yet additional embodiments, identifying a patient in need of neurogenesis modulation comprises selecting a population or sub-population of patients, or an individual patient, that is more amenable to treatment and/or less susceptible to side effects than other patients having the same disease or condition. In some embodiments, identifying a patient amenable to treatment with mesembrenone comprises identifying a patient who has been exposed to a factor known to enhance neurogenesis, including but not limited to, exercise, hormones or other endogenous factors, and drugs taken as part of a pre-existing treatment regimen. In some embodiments, a sub-population of patients is identified as being more amenable to neurogenesis modulation with mesembrenone or a pharmaceutically acceptable salt thereof by taking a cell or tissue sample from prospective patients, isolating and culturing neural cells from the sample, and determining the effect of the compound on the degree or nature of neurogenesis of the cells, thereby allowing selection of patients for which the therapeutic agent has a substantial effect on neurogenesis. Advantageously, the selection of a patient or population of patients in need of or amenable to treatment with mesembrenone according to the invention allows more effective treatment of the disease or condition targeted for treatment.

In some embodiments, the patient has suffered a CNS insult, such as a CNS lesion, a seizure (e.g., electroconvulsive seizure treatment; epileptic seizures), radiation, chemotherapy and/or stroke or other ischemic injury. Without being bound by any particular theory, and offered to improve understanding of the invention, it is believed that some CNS insults/injuries leads to increased proliferation of neural stem cells, but that the resulting neural cells form aberrant connections which can lead to impaired CNS function and/or diseases, such as temporal lobe epilepsy. According to the invention, a therapeutically effective amount of mesembrenone or a pharmaceutically acceptable salt thereof is administered to a patient who has suffered, or is at risk of suffering, a CNS insult or injury to stimulate neurogenesis. Advantageously, stimulation of the differentiation of neural stem cells with mesembrenone, optionally in combination with one or more other neurogenic agents, activates signalling pathways necessary for progenitor cells to effectively migrate and incorporate into existing neural networks or to block inappropriate proliferation.

Opiate or Opioid Based Analgesic

Additionally, the invention provides for the application of mesembrenone or a pharmaceutically acceptable salt thereof to treat a subject or patient for a condition due to the anti-neurogenic effects of an opiate or opioid based analgesic. In some embodiments, the administration of an opiate or opioid based analgesic, such as an opiate like morphine or other opioid receptor agonists, to a subject or patient, results in a decrease in, or inhibition of, neurogenesis. The administration of mesembrenone with an opiate or opioid based analgesic would reduce the anti-neurogenic effect. One non-limiting example is administration of such a combination with an opioid receptor agonist after surgery (such as for treating post-operative pain).

Accordingly there is provided a method of treating post operative pain in a subject or patient by combining administration of an opiate or opioid based analgesic with mesembrenone or a pharmaceutically acceptable salt thereof.

Other embodiments include a method to treat or prevent decreases in, or inhibition of, neurogenesis in other cases involving use of an opioid receptor agonist, comprising administering a therapeutically effective amount of mesembrenone or a pharmaceutically acceptable salt thereof as described herein. Non-limiting examples include cases involving an opioid receptor agonist, which decreases or inhibits neurogenesis, and drug addiction, drug rehabilitation, and/or prevention of relapse into addiction. In some embodiments, the opioid receptor agonist is morphine, opium or another opiate.

In further embodiments, the invention includes a method to treat a cell, tissue, or subject which is exhibiting decreased neurogenesis or increased neurodegeneration. In some cases, the cell, tissue, or subject is, or has been, subjected to, or contacted with, an agent that decreases or inhibits neurogenesis. One non-limiting example is a human subject that has been administered morphine or other agent which decreases or inhibits neurogenesis. Non-limiting examples of other agents include opiates and opioid receptor agonists, such as mu receptor subtype agonists, that inhibit or decrease neurogenesis.

Thus in additional embodiments, the methods may be used to treat subjects having, or diagnosed with, depression or other withdrawal symptoms from morphine or other agents which decrease or inhibit neurogenesis. This is distinct from the treatment of subjects having, or diagnosed with, depression independent of an opiate, such as that of a psychiatric nature, as disclosed herein. In further embodiments, the method may be used to treat a subject with one or more chemical addictions or dependencies, such as with morphine or other opiates, where the addiction or dependency is ameliorated or alleviated by an increase in neurogenesis.

The amount of mesembrenone or a pharmaceutically acceptable salt thereof may be such that it results in a measurable relief of a disease condition like those described herein. As a non-limiting example, an improvement in the Hamilton depression scale (HAM-D) score for depression may be used to determine (such as quantitatively) or detect (such as qualitatively) a measurable level of improvement in the depression of a subject.

Non-limiting examples of symptoms that may be treated according to the invention herein include abnormal behavior, abnormal movement, hyperactivity, hallucinations, acute delusions, combativeness, hostility, negativism, withdrawal, seclusion, memory defects, sensory defects, cognitive defects, and tension. Non-limiting examples of abnormal behavior include irritability, poor impulse control, distractibility, and aggressiveness. Outcomes from treatment according to the invention include improvements in cognitive function or capability in comparison to the absence of treatment.

Additional examples of diseases and conditions treatable by the method according to the invention include, but are not limited to, neurodegenerative disorders and neural disease, such as dementias (e.g., senile dementia, memory disturbances/memory loss, dementias caused by neurodegenerative disorders (e.g., Alzheimer's, Parkinson's disease or disorders, Huntington's disease (Huntington's Chorea), Lou Gehrig's disease, multiple sclerosis, Pick's disease, Parkinsonism dementia syndrome), progressive subcortical gliosis, progressive supranuclear palsy, thalmic degeneration syndrome, hereditary aphasia, amyotrophic lateral sclerosis, Shy-Drager syndrome, and Lewy body disease; vascular conditions (e.g., infarcts, hemorrhage, cardiac disorders); mixed vascular and Alzheimer's; bacterial meningitis; Creutzfeld-Jacob Disease; and Cushing's disease.

The disclosed embodiments also provide for the treatment of a nervous system disorder related to neural damage, cellular degeneration, a psychiatric condition, cellular (neurological) trauma and/or injury (e.g., subdural hematoma or traumatic brain injury), toxic chemicals (e.g., heavy metals, alcohol, some medications), CNS hypoxia, or other neurologically related conditions. In practice, the disclosed methods may be applied to a subject or patient afflicted with, or diagnosed with, one or more central or peripheral nervous system disorders in any combination. Diagnosis may be performed by a skilled person in the applicable fields using known and routine methodologies which identify and/or distinguish these nervous system disorders from other conditions.

Non-limiting examples of nervous system disorders related to cellular degeneration include neurodegenerative disorders, neural stem cell disorders, neural progenitor cell disorders, degenerative diseases of the retina, and ischemic disorders. In some embodiments, an ischemic disorder comprises an insufficiency, or lack, of oxygen or angiogenesis, and non-limiting example include spinal ischemia, ischemic stroke, cerebral infarction, multi-infarct dementia. While these conditions may be present individually in a subject or patient, the disclosed methods also provide for the treatment of a subject or patient afflicted with, or diagnosed with, more than one of these conditions in any combination.

Non-limiting embodiments of nervous system disorders related to a psychiatric condition include neuropsychiatric disorders and affective disorders. As used herein, an affective disorder refers to a disorder of mood such as, but not limited to, depression, post-traumatic stress disorder (PTSD), hypomania, panic attacks, excessive elation, bipolar depression, bipolar disorder (maniac-depression), and seasonal mood (or affective) disorder. Other non-limiting embodiments include schizophrenia and other psychoses, lissencephaly syndrome, anxiety syndromes, anxiety disorders, phobias, stress and related syndromes (e.g., panic disorder, phobias, adjustment disorders, migraines), cognitive function disorders, aggression, drug and alcohol abuse, drug addiction, and drug-induced neurological damage, obsessive compulsive behavior syndromes, borderline personality disorder, non-senile dementia, post-pain depression, post-partum depression, and cerebral palsy.

Examples of nervous system disorders related to cellular or tissue trauma and/or injury include, but are not limited to, neurological traumas and injuries, surgery related trauma and/or injury, retinal injury and trauma, injury related to epilepsy, cord injury, spinal cord injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxin, and spinal cord injury related to environmental toxin.

Non-limiting examples of nervous system disorders related to other neurologically related conditions include learning disorders, memory disorders, age-associated memory impairment (AAMI) or age-related memory loss, autism, learning or attention deficit disorders (ADD or attention deficit hyperactivity disorder, ADHD), narcolepsy, sleep disorders and sleep deprivation (e.g., insomnia, chronic fatigue syndrome), cognitive disorders, epilepsy, injury related to epilepsy, and temporal lobe epilepsy.

Other non-limiting examples of diseases and conditions treatable by a method of the invention includes, but is not limited to, hormonal changes (e.g., depression and other mood disorders associated with puberty, pregnancy, or aging (e.g., menopause)); and lack of exercise (e.g., depression or other mental disorders in elderly, paralyzed, or physically handicapped patients); infections (e.g., HIV); genetic abnormalities (down syndrome); metabolic abnormalities (e.g., vitamin B12 or folate deficiency); hydrocephalus; memory loss separate from dementia, including mild cognitive impairment (MCI), age-related cognitive decline, and memory loss resulting from the use of general anesthetics, chemotherapy, radiation treatment, post-surgical trauma, or therapeutic intervention; and diseases of the of the peripheral nervous system (PNS), including but not limited to, PNS neuropathies (e.g., vascular neuropathies, diabetic neuropathies, amyloid neuropathies, and the like), neuralgias, neoplasms, myelin-related diseases, etc and the treatment of, or supportive management of, subjective stress in healthy individuals The advantages of a dual PDE4 and 5-HT uptake inhibition mechanisms of action include the possibility of using a lower dose to achieve the same therapeutic objective in conditions that respond to both a 5-HT uptake inhibitor, as well as a PDE4 inhibitor, such as conditions that modulate neurogenesis. The use of lower doses of the dual acting mesembrenone can be expected to have a reduced side-effect profile than single-action pharmaceuticals or medicaments, such as a reduction in the loss of libido commonly found with in 5-HT uptake inhibitors; and a reduction in the nausea and vomiting found with PDE4 inhibitors. The dual action of the pharmaceutical or medicament can be an advantage by reducing the number of medications that have to be taken where there is a relevant co-morbidity. For example arthritis together with depression, Alzheimers together with depression.

For the above uses, the required dosage will of course vary depending on the mode of administration, the particular condition to be treated and the effect desired. An indicated daily dosage in the larger mammal, e.g. humans, is in the range from about 5 micrograms to 5 milligrams mesembrenone, preferably from 20 micrograms to 200 micrograms mesembrenone, conveniently administered for example in divided doses up to four times a day or in slow release form. Suitable unit dosage forms comprise from about 5 micrograms to 500 micrograms, preferably 20 micrograms to 100 micrograms of mesembrenone.

Mesembrenone may be administered in free form or in pharmaceutically acceptable salt form, e.g. as indicated above. Such salts may be prepared by conventional manner and exhibit the same order of activity as mesembrenone in free form.

Mesembrenone or a pharmaceutically acceptable salt thereof may be formulated in the form of a pharmaceutical composition according to a method known in the art, e.g. by mixing with one or more pharmaceutically acceptable carrier or diluent.

Mesembrenone or a pharmaceutically acceptable salt thereof may be administered by any conventional route, in particular enterally, e.g. orally, e.g. in the form of aqueous-ethanolic tinctures, tablets, capsules, softgels, oral sprays, gums, wafers or a sub-lingual preparations, nasally, e.g. in the form of nasal sprays or inhalers, or transdermally, e.g. in the form of skin patches, lotions, creams, and ointments.

In accordance with the foregoing, the present invention further provides:
a) the use of mesembrenone or a pharmaceutically acceptable salt thereof as a PDE4 modulator or inhibitor or as a dual PDE4 and 5-HT uptake inhibitor, e.g. in any of the particular indications hereinbefore set forth; or
b) the use of mesembrenone or a pharmaceutically acceptable salt thereof, in the manufacture of a medicament, for the treatment or inhibition or prevention of any of the indications hereinbefore set forth, including, but not limited to, the treatment of conditions of the central and peripheral nervous system that respond to stimulating or increasing neurogenesis; or
c) a pharmaceutical composition, for use in any of the indications hereinbefore set forth, comprising mesembrenone or a pharmaceutically acceptable salt thereof together with one or more pharmaceutically acceptable diluents or carriers therefore; or
d) a method of preventing, alleviating, treating, modulating, improving, stabilizing, enhancing a disorder, a condition or a disease as disclosed hereinbefore.

DESCRIPTION OF THE INVENTION

The invention is now described according to the following non-limiting examples and methods and with reference to the following diagrammatic drawings.

In the drawings:

FIG. 2 represents the concentration—response curve of mesembrenone on both the 5-HT transporter and PDE-4B enzyme at different concentrations.

Isolation of Mesembrenone

Figure 1:
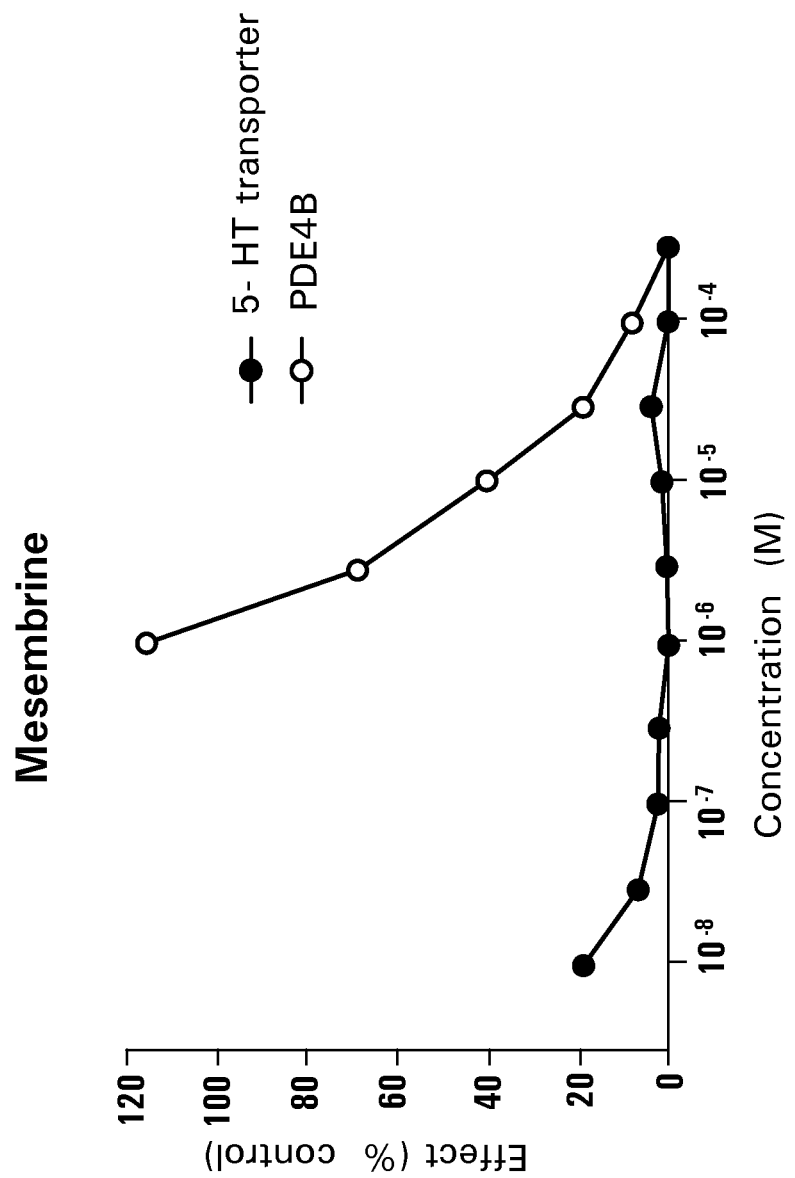
FIG. 1 represents the concentration—response curve of mesembrine on both the 5-HT transporter and PDE-4B enzyme at different concentrations.

The aerial parts of *S. tortuosum* were dried and pulverized. The material was submerged in distilled water and acidified by adding 4% $H_2SO_4$. To this water phase 20% $NH_4OH$ was added to basify the solution followed by excessive extraction with dichloromethane. This crude alkaloid extract was adsorbed on silica gel and loaded on a silica gel 60F column eluting with 100% $CH_2Cl_2$ and thereafter with $CH_2Cl_2$/EtOAc (8:2) with increasing polarity to $CH_2Cl_2$/EtOAc/MeOH (7:2:1). 35 serial 100 mL eluted fractions were collected and the purity assessed for each fraction using thin layer chromatography. The purest fractions were then selected, and GC-MS used (Agilent 6890N GC equipped with a HP-5MS 5% phenyl methyl siloxane column (30 m×250 µm i.d.×0.25 µm capillary column)) to identity mesembrenone according to the published fragmentation pattern. Fractions rich in mesembrenone were pooled, and re-adsorbed on silica gel. The pooled sample was then fractionated on a silica gel 60F column eluting with $CH_2Cl_2$/EtOAc (8:2). The purity of the pooled fraction was followed on GC-MS (Agilent 6890N GC) equipped with a HP-5MS 5% phenyl methyl siloxane column (30 m×250 µm i.d.×0.25 µm capillary column). The oven temperature program: 60° C., rising to 255° C. at a rate of 20° C./min and held for 15 min. Helium was used as carrier gas. Spectra obtained on electron impact at 70 eV, scanning from 35 to 550 m/z. Under these conditions mesembrenone had a rt of 18.8 min, and a sample isolated. The structure of the sample was confirmed as mesembrenone using NMR.

Use of Mesembrenone

A sample of pure mesembrenone isolated from *Sceletium* plant material as discussed above is tested in binding studies at a range of concentrations in-vitro for 5-HT transporter inhibitory activity (i.e. serotonin-uptake inhibition), and at a range of concentrations in-vitro for PDE-4B enzyme inhibitory activity. For comparison, a sample of pure mesembrine is tested in-vitro for PDE-4B inhibitory activity, across a range of concentrations set out in Tables 1 to 4 and in FIGS. 1 and 2.

TABLE 1

Mesembrenone binding studies on the 5-HT transporter.
The control compound is imipramine.

| Test Concentration (M) | % of Control Specific Binding (Average of n = 2) |
| --- | --- |
| 1.0E−08 | 96.4 |
| 3.0E−08 | 72.7 |
| 1.0E−07 | 44.9 |
| 3.0E−07 | 16.4 |
| 1.0E−06 | 9.4 |
| 3.0E−06 | 0.6 |
| 1.0E−08 | 18.6 |
| 3.0E−08 | 7.0 |
| 1.0E−07 | 2.0 |
| 3.0E−07 | 1.7 |
| 1.0E−06 | −0.7 |
| 1.0E−06 | 0.9 |
| 3.0E−06 | −0.8 |
| 3.0E−06 | 0.1 |
| 1.0E−05 | 1.1 |
| 3.0E−05 | 3.2 |
| 1.0E−04 | −0.2 |
| 3.0E−04 | 0.2 |

†General Procedures

| Assay | Origin | Reference Compound | Bibliography |
|---|---|---|---|
| 5-HT transporter (h) | Human recombinant (CHO cells) | Imipramine | Tatsumi et al. (1999)[(4)] |

[(4)]TATSUMI, M., JANSEN, K., BLAKELY, R.D. and RICHELSON, E. (1999) Pharmacological profile of neuroleptics at human monoamine transporters. Eur. J. Pharmacol., 368: 277-283.

Experimental Conditions

| Assay | Ligand | Conc. | Non Specific | Incubation | Method of Detection |
|---|---|---|---|---|---|
| 5-HT transporter (h) | [³H]imipramine | 2 nM | imipramine (10 µM) | 60 min./ 22° C. | Scintillation counting |

Analysis and Expression of Results

The specific ligand binding to the receptors is defined as the difference between the total binding and the nonspecific binding determined in the presence of an excess of unlabelled ligand.

The results are expressed as a percent of control specific binding ((measured specific binding/control specific binding)×100) obtained in the presence of mesembrenone.

The $IC_{50}$ values (concentration causing a half-maximal inhibition of control specific binding) and Hill coefficients (nH) are determined by non-linear regression analysis of the competition curves generated with mean replicate values using Hill equation curve fitting $(Y=D+[(A-D)/(1+(C/C_{50})^{nH})])$, where Y=specific binding, D=minimum specific binding, A=maximum specific binding, C=compound concentration, $C_{50}=IC_{50}$, and nH=slope factor).

TABLE 2

PDE 4 inhibition for mesembrenone.
The control compound is rolipram.

| Test Concentration (M) | % of Control Specific Activity (Average of n = 2) |
|---|---|
| 1.0E−08 | 94.4 |
| 3.0E−08 | 89.3 |
| 1.0E−07 | 80.1 |
| 3.0E−07 | 56.2 |
| 1.0E−06 | 37.5 |
| 3.0E−06 | 16.7 |

TABLE 3

PDE 4 inhibition for mesembrine.
The control compound was rolipram.

| Test Concentration (M) | % of Control Specific Activity (Average of n = 2) |
|---|---|
| 1.0E−06 | 114.6 |
| 3.0E−06 | 68.3 |
| 1.0E−05 | 40.3 |
| 3.0E−05 | 19.2 |
| 1.0E−04 | 8.5 |
| 3.0E−04 | −1.6 |

‡General Procedure

| Assay | Origin | Reference Compound | Bibliography |
|---|---|---|---|
| PDE4B (h) | human recombinant (Sf9 cells) | Rolipram | Saldou et al. (1998)[(B)] |

[(B)]SALDOU, N., OBERNOLTE, R., HUBER, A., BADCKER, P.A., WILHELM, R., ALVAREZ, R., LI, B., XIA, L., CALLAN, O., SU, C., JARNAGIN, K. and SHELTON, E.R. (1998), Comparison of recombinant human PDE4 isoforms: interaction with substrate and inhibitors. Cell Signal., 10: 427-440.

Experimental Conditions

| Assay | Substrate | Incubation | Reaction Product | Method of Detection |
|---|---|---|---|---|
| PDE4B (h) | cAMP (40 nM) | 30 min./22° C. | residual AMPc | HTRF |

Analysis and Expression of Results

The results are expressed as a percent of control specific activity ((measured specific activity/control specific activity)×100) obtained in the presence of mesembrenone.

The $IC_{50}$ values (concentration causing a half-maximal inhibition of control specific activity) and Hill coefficients (nH) are determined by non-linear regression analysis of the inhibition curves generated with mean replicate values using Hill equation curve fitting $(Y=D+[(A-D)/(1+(C/C_{50})^{nH})])$, where Y=specific activity, D=minimum specific activity, A=maximum specific activity, C=compound concentration, $C_{50}=IC_{50}$, and nH=slope factor).

TABLE 4

Summary of results for mesembrine and mesembrenone on the 5-HT tranporter and on PDE4B.

| | 5-HT transporter | | PDE4B | |
|---|---|---|---|---|
| Compound | Ki (nM) | $n_H$ | IC50 (nM) | $n_H$ |
| mesembrine | 1.4* | 1.0* | 7800 | 1.3 |
| mesembrenone | 27 | 1.0 | 470 | 0.8 |

$n_H$ = Hill coefficient
*this value has been extrapolated from the dose-response curve shown in FIGS. 1 and 2.

The results confirm that mesembrenone is an inhibitor of the 5-HT transporter, and unexpectedly demonstrates the novel finding of its potent PDE4 inhibitory properties The difference between concentrations for a 50% inhibitory effect on the two assays is only 17 times for mesembrenone, whereas it is 5500 for mesembrine. Thus mesembrenone can be regarded as being a "dual-acting" inhibitor, simultaneously acting as a 5-HT transporter inhibitor as well as a PDE4 inhibitor. By comparison mesembrine is highly selective for the inhibition of the 5-HT transporter relative to the inhibition of PDE4B.

The invention claimed is:

1. A method of modulating PDE-4 activity in an individual, comprising administering to the individual mesembrenone or a pharmaceutically acceptable salt thereof.

2. The method of claim 1, wherein the mesembrenone is extracted and isolated from plant material of the plant family Mesembryanthemaceae.

3. The method of claim 1, wherein the mesembrenone is in the form of a plant extract from plant material of the plant family Mesembryanthemaceae.

4. The method of claim 3, where the mesembrenone is obtained from plant material of a plant or plants of the genus *Sceletium*.

5. The method of claim 4, wherein the mesembrenone is obtained from plant material of a plant or plants of the species *Sceletium tortuosum*(L.) N.E.Br.

6. The method of claim 1, wherein the mesembrenone or the pharmaceutically acceptable salt thereof is administered as a dietary supplement.

7. A method of inhibiting PDE-4 activitiy in an individual, comprising administering to the individual mesembrenone, or a pharmaceutically acceptable salt thereof.

8. A method of inhibiting PDE-4 activity and 5HT-uptake in an individual, comprising administering to the individual mesembrenone, or a pharmaceutically acceptable salt thereof.

9. The method of claim 1, wherein the individual is a healthy individual.

10. The method of claim 7, wherein the mesembrenone is extracted and isolated from plant material of the plant family Mesembryanthemaceae.

11. The method of claim 7, wherein the mesembrenone is in the form of a plant extract from plant material of the plant family Mesembryanthemaceae.

12. The method of claim 7, wherein the mesembrenone is obtained from plant material of a plant or plants of the genus *Sceletium*.

13. The method of claim 7, wherein the mesembrenone is obtained from plant material of a plant or plants of the species *Sceletium tortuosum*(L.) N.E.Br.

14. The method of claim 7, wherein the individual is a healthy individual.

15. The method of claim 8, wherein the mesembrenone is extracted and isolated from plant material of the plant family Mesembryanthemaceae.

16. The method of claim 8, wherein the mesembrenone is in the form of a plant extract from plant material of the plant family Mesembryanthemaceae.

17. The method of claim 8, wherein the mesembrenone is obtained from plant material of a plant or plants of the genus *Sceletium*.

18. The method of claim 8, wherein the mesembrenone is obtained from plant material of a plant or plants of the species *Sceletium tortuosum*(L.) N.E.Br.

19. The method of claim 8, wherein the individual is a healthy individual.

* * * * *